United States Patent
Gamelsky et al.

(10) Patent No.: US 6,238,344 B1
(45) Date of Patent: May 29, 2001

(54) MEDICAL DIAGNOSTIC ULTRASOUND IMAGING SYSTEM WITH A WIRELESSLY-CONTROLLED PERIPHERAL

(75) Inventors: Jeff N. Gamelsky; James B. Hutchison, both of Palo Alto; Dermot P. McCartan, Sunnyvale, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/538,449

(22) Filed: Mar. 30, 2000

(51) Int. Cl.[7] .................................................. A61B 08/00
(52) U.S. Cl. ............................................ 600/437; 128/903
(58) Field of Search ................................. 600/437, 438, 600/447, 459, 443

(56) References Cited

U.S. PATENT DOCUMENTS

| | | |
|---|---|---|
| 3,972,320 | 8/1976 | Kalman . |
| 4,100,916 | 7/1978 | King . |
| 4,413,629 | 11/1983 | Durley, III . |
| 4,522,213 | 6/1985 | Wallroth et al. . |
| 4,974,607 | 12/1990 | Miwa . |
| 5,291,399 | 3/1994 | Chaco . |
| 5,603,323 | 2/1997 | Pflugrath et al. . |
| 5,640,960 | 6/1997 | Jones et al. . |
| 5,715,823 | 2/1998 | Wood et al. . |
| 5,778,177 | 7/1998 | Azar . |
| 5,851,186 | 12/1998 | Wood et al. . |
| 5,865,733 | * 2/1999 | Malinouskas et al. ............ 600/300 |
| 5,867,821 | 2/1999 | Ballantyne et al. . |
| 5,891,035 | 4/1999 | Wood et al. . |
| 5,944,659 | 8/1999 | Flach et al. . |
| 5,957,854 | * 9/1999 | Besson et al. ..................... 600/509 |
| 5,964,709 | 10/1999 | Chiang et al. . |

FOREIGN PATENT DOCUMENTS

0123456 A2 * 1/2000 (EP) ................................ 100/100

* cited by examiner

Primary Examiner—Marvin M. Lateef
Assistant Examiner—Maulin Patel
(74) Attorney, Agent, or Firm—Brinks Hofer Gilson & Lione

(57) ABSTRACT

The preferred embodiments described herein provide a medical diagnostic ultrasound imaging system with a wirelessly-controlled peripheral. In one preferred embodiment, an ultrasound imaging system transmits a peripheral command to an ultrasound peripheral via a first wireless communication device, and the peripheral receives the command via a second wireless communication device. The peripheral performs an operation in response to the receipt of the command. Data is communicated between the ultrasound system and the peripheral via a data transmission medium that physically couples the ultrasound system and peripheral. With this preferred embodiment, an ultrasound system can control a peripheral without the disadvantages associated with current ultrasound system-peripheral configurations.

35 Claims, 5 Drawing Sheets

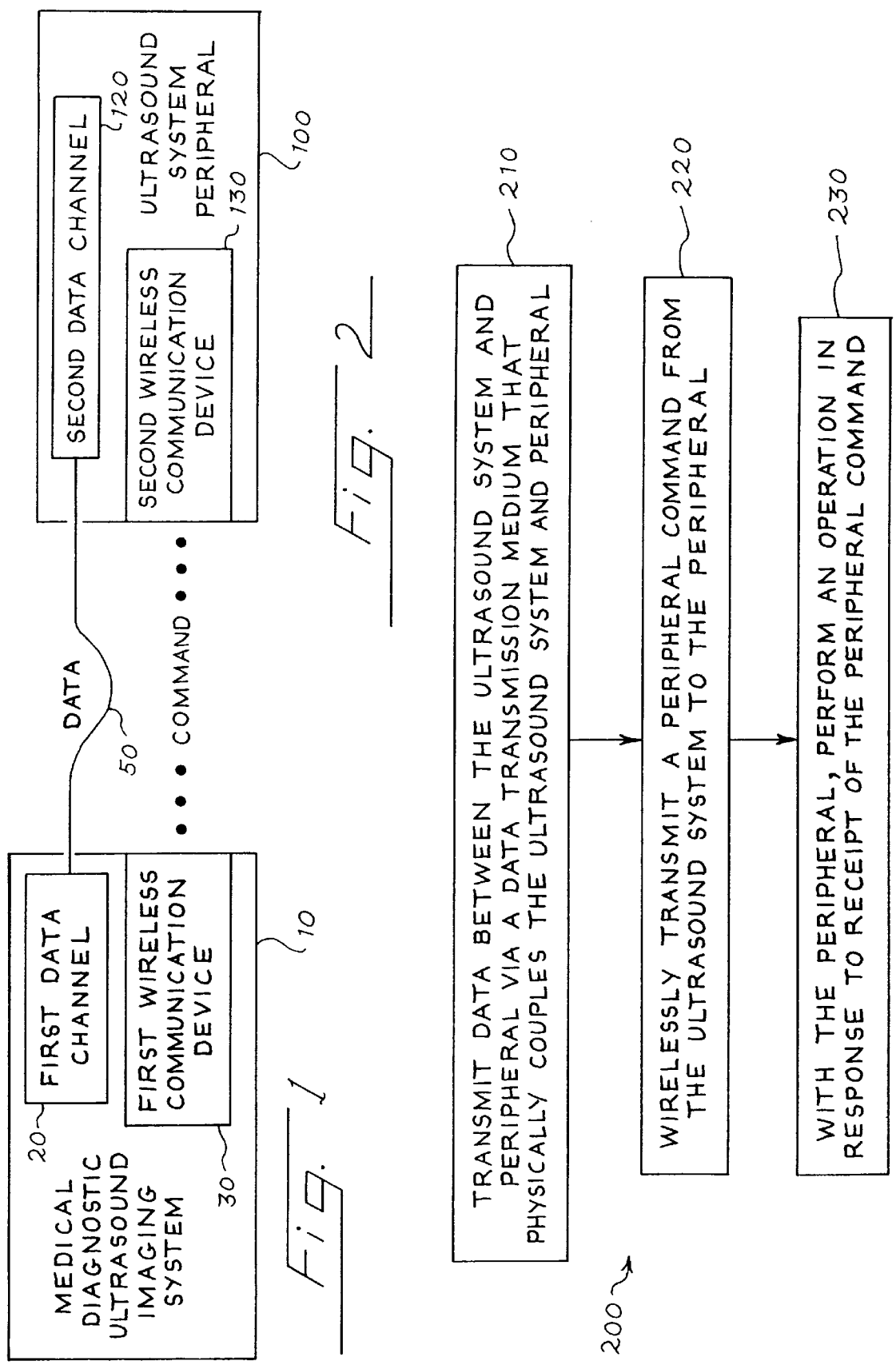

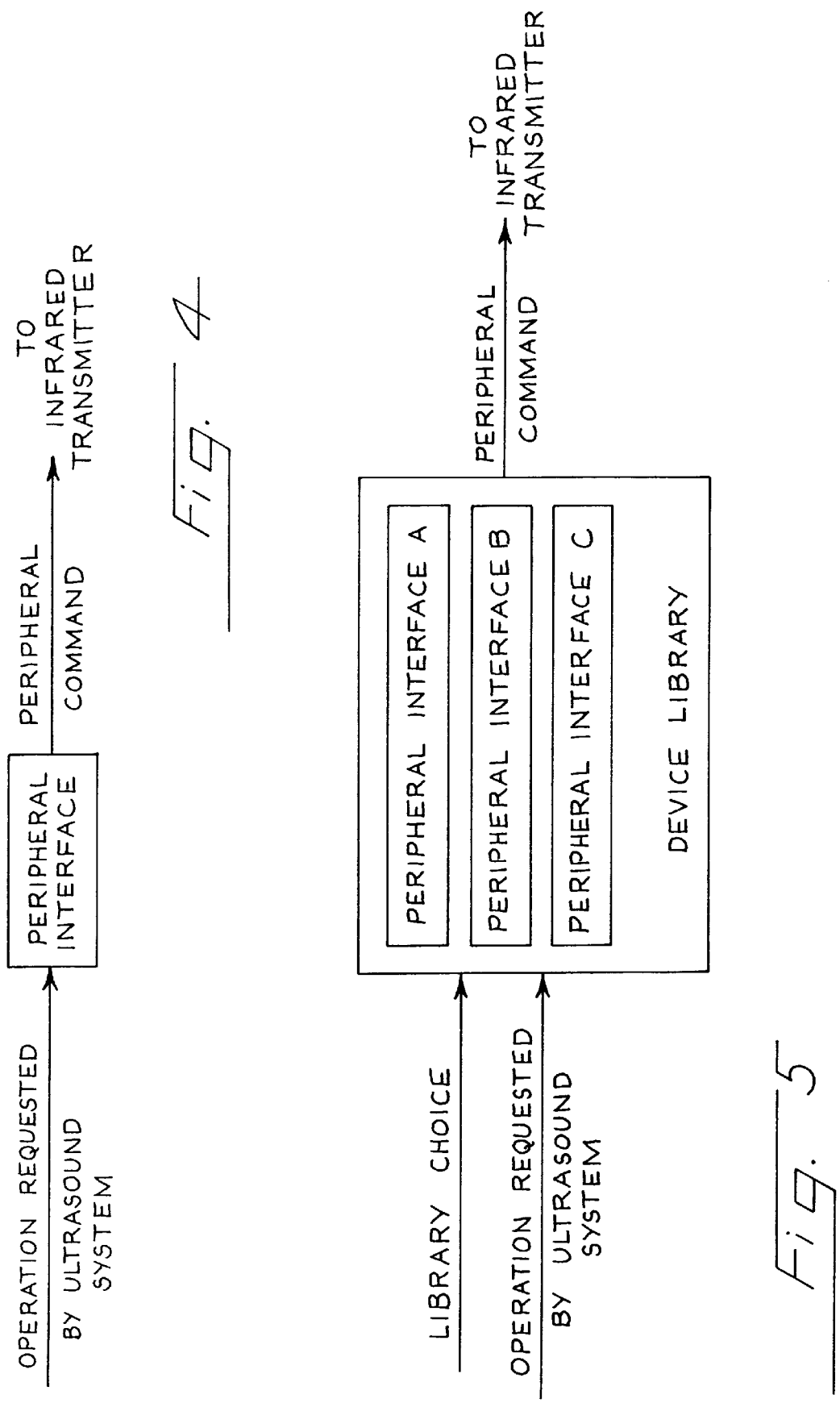

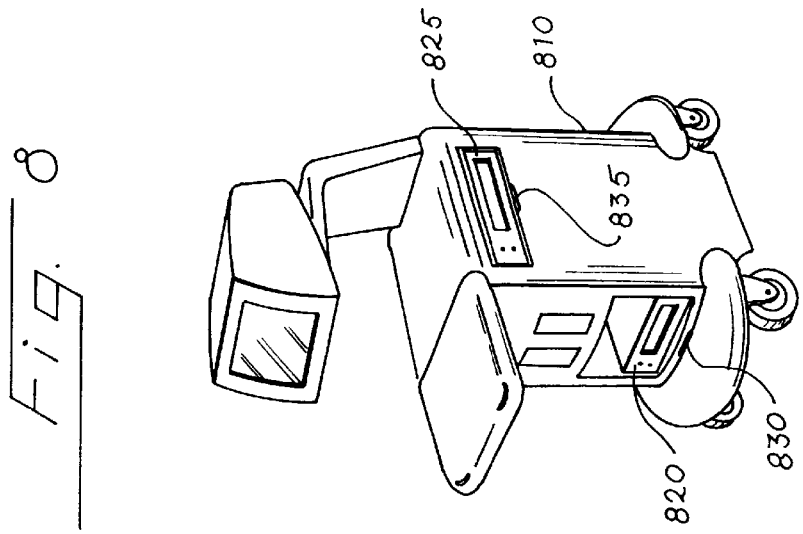
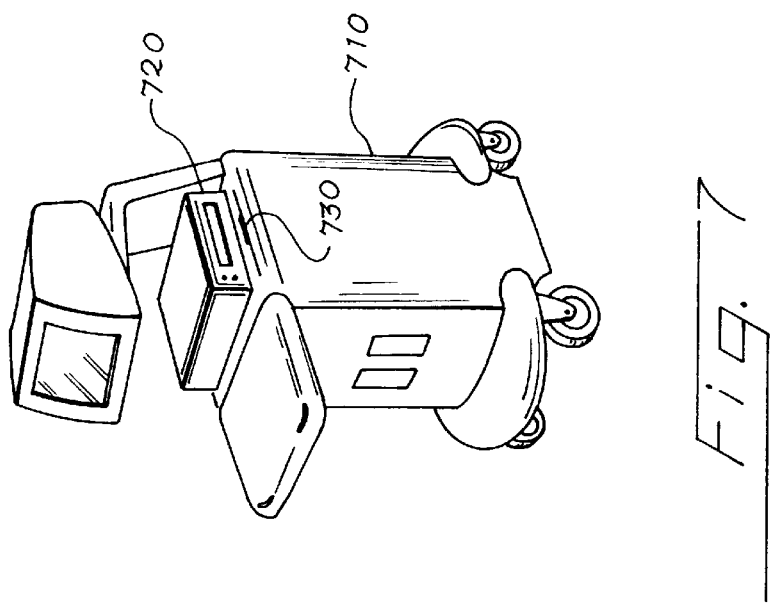
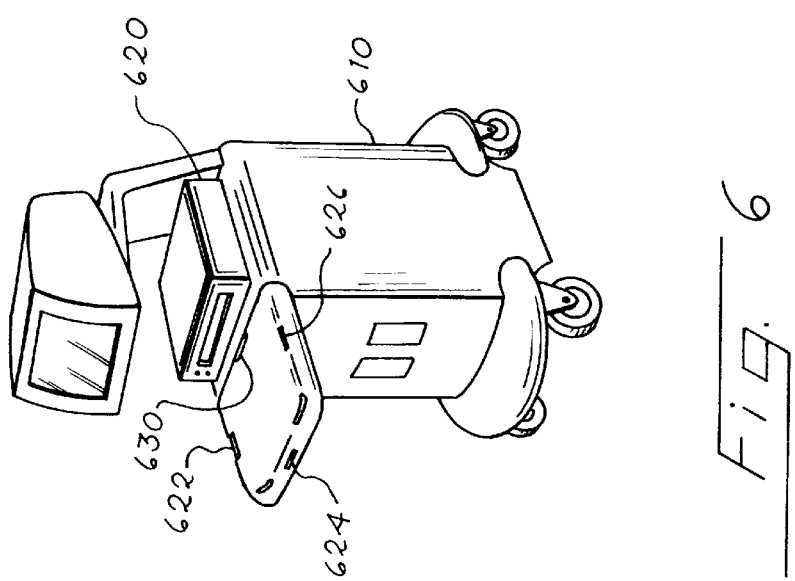

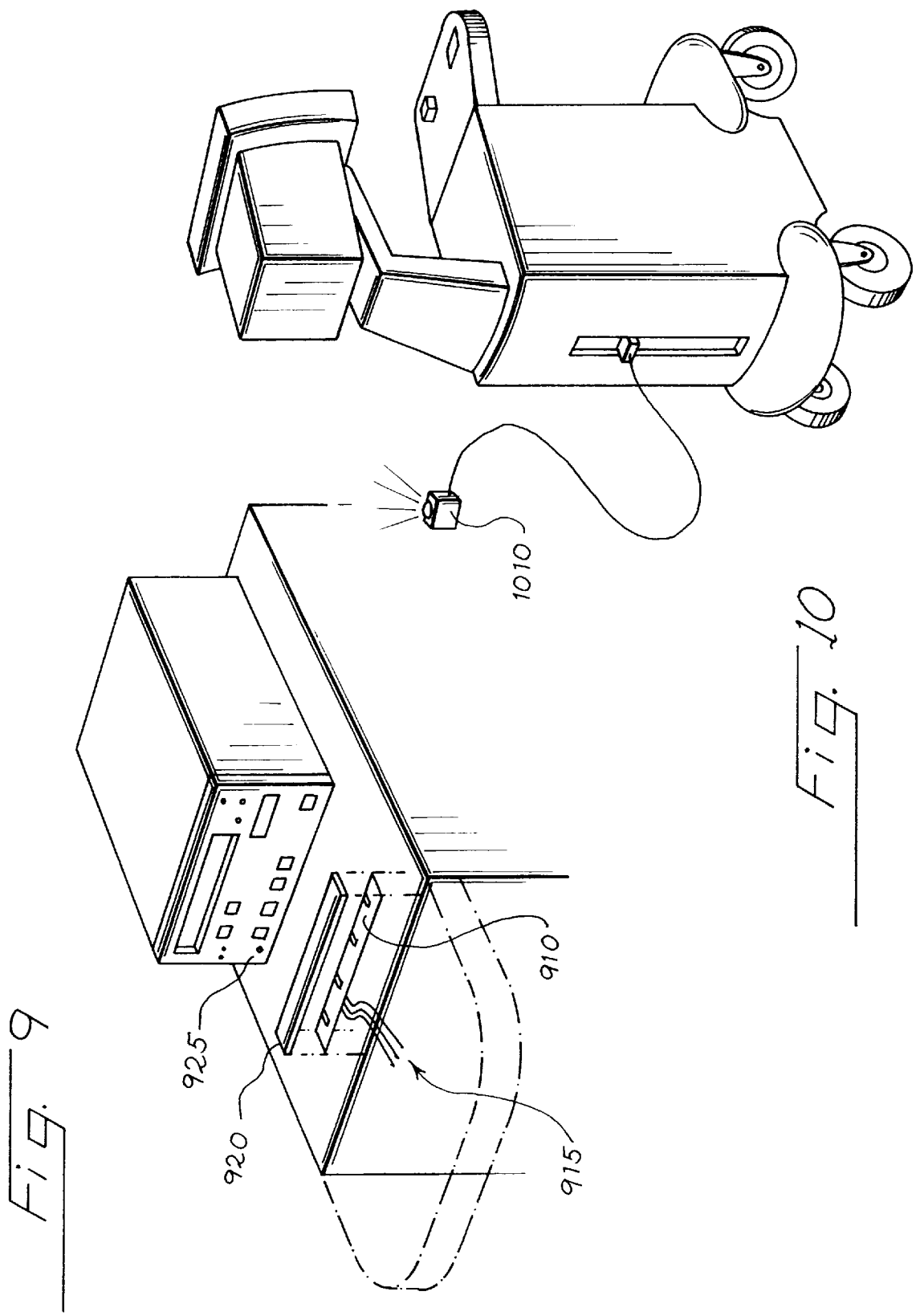

MEDICAL DIAGNOSTIC ULTRASOUND IMAGING SYSTEM WITH A WIRELESSLY-CONTROLLED PERIPHERAL

BACKGROUND

Many medical diagnostic ultrasound imaging applications use a peripheral device in conjunction with an ultrasound system. For example, a videocassette recorder ("VCR") is often used to store a generated image for later analysis. Typically, each peripheral that is used with an ultrasound system has a wired or hard-wired command port to allow the ultrasound system to send commands to the peripheral. For example, specialized VCRs (such as SONY® SVO9500MD or PANASONIC® AG-MD830) contain a wired or hard-wired command port in addition to a data port (e.g., a video/audio I/O port). A command cable connects the command ports (e.g., RS-232 ports), and a data cable connects the data ports of the ultrasound system and peripheral. To record a generated image on videotape, the ultrasound system sends video data to the VCR via the data cable and sends a "record" command to the VCR via the command cable. When the VCR receives the "record" command from the ultrasound system, it performs a record operation to record the incoming video data on videotape.

There are several disadvantages associated with the current system-peripheral configuration. Ultrasound systems typically require a single command port for each peripheral used with the system. Because there is a limited number of command ports on an ultrasound system, this requirement can limit the number of peripherals that can be used with the ultrasound system. In addition to this physical-resource limitation, the use of multiple command ports increases the cost of the ultrasound system. The current configuration also results in increased costs for peripherals because of the need for a separate command port to receive commands from the ultrasound system. For example, consumer-grade VCRs can be much less expensive than VCRs with a wired or hard-wired command port.

There is, therefore, a need for a medical diagnostic ultrasound imaging system and peripheral that will overcome the disadvantages described above.

SUMMARY

The present invention is defined by the following claims, and nothing in this section should be taken as a limitation on those claims.

By way of introduction, the preferred embodiments described below provide a medical diagnostic ultrasound imaging system with a wirelessly-controlled peripheral. In one preferred embodiment, an ultrasound imaging system transmits a peripheral command to an ultrasound peripheral via a first wireless communication device, and the peripheral receives the command via a second wireless communication device. The peripheral performs an operation in response to the receipt of the command. Data is communicated between the ultrasound system and the peripheral via a data transmission medium that physically couples the ultrasound system and peripheral. With this preferred embodiment, an ultrasound system can control a peripheral without the disadvantages associated with current ultrasound system-peripheral configurations.

The preferred embodiments will now be described with reference to the attached drawings.

BRIEF DESCRIPTION OF THE DRAWINGS

FIG. 1 is a block diagram of a medical diagnostic ultrasound imaging system and an ultrasound system peripheral of a preferred embodiment.

FIG. 2 is a flow chart of a method of communicating data and peripheral commands between a medical diagnostic ultrasound imaging system and an ultrasound system peripheral of a preferred embodiment.

FIG. 4 is a block diagram illustrating a peripheral interface of a preferred embodiment.

FIG. 5 is a block diagram illustrating a device library of a preferred embodiment.

FIG. 6 is an illustration of an ultrasound system of a preferred embodiment in which a forward-facing VCR is positioned on a top surface of an ultrasound system housing.

FIG. 7 is an illustration of an ultrasound system of a preferred embodiment in which a side-facing VCR is positioned on a top surface of an ultrasound system housing.

FIG. 8 is an illustration of an ultrasound system of a preferred embodiment in which two VCRs are positioned in openings formed in an ultrasound system housing.

FIG. 9 is an illustration of an ultrasound system of a preferred embodiment in which an infrared transmitter is integrally mounted in a housing of the ultrasound system.

FIG. 10 is an illustration of an ultrasound system of a preferred embodiment in which a wireless communication device is coupled with the system by a cable and is not integral to the ultrasound system housing.

DETAILED DESCRIPTION OF THE PRESENTLY PREFERRED EMBODIMENTS

Figure 3:
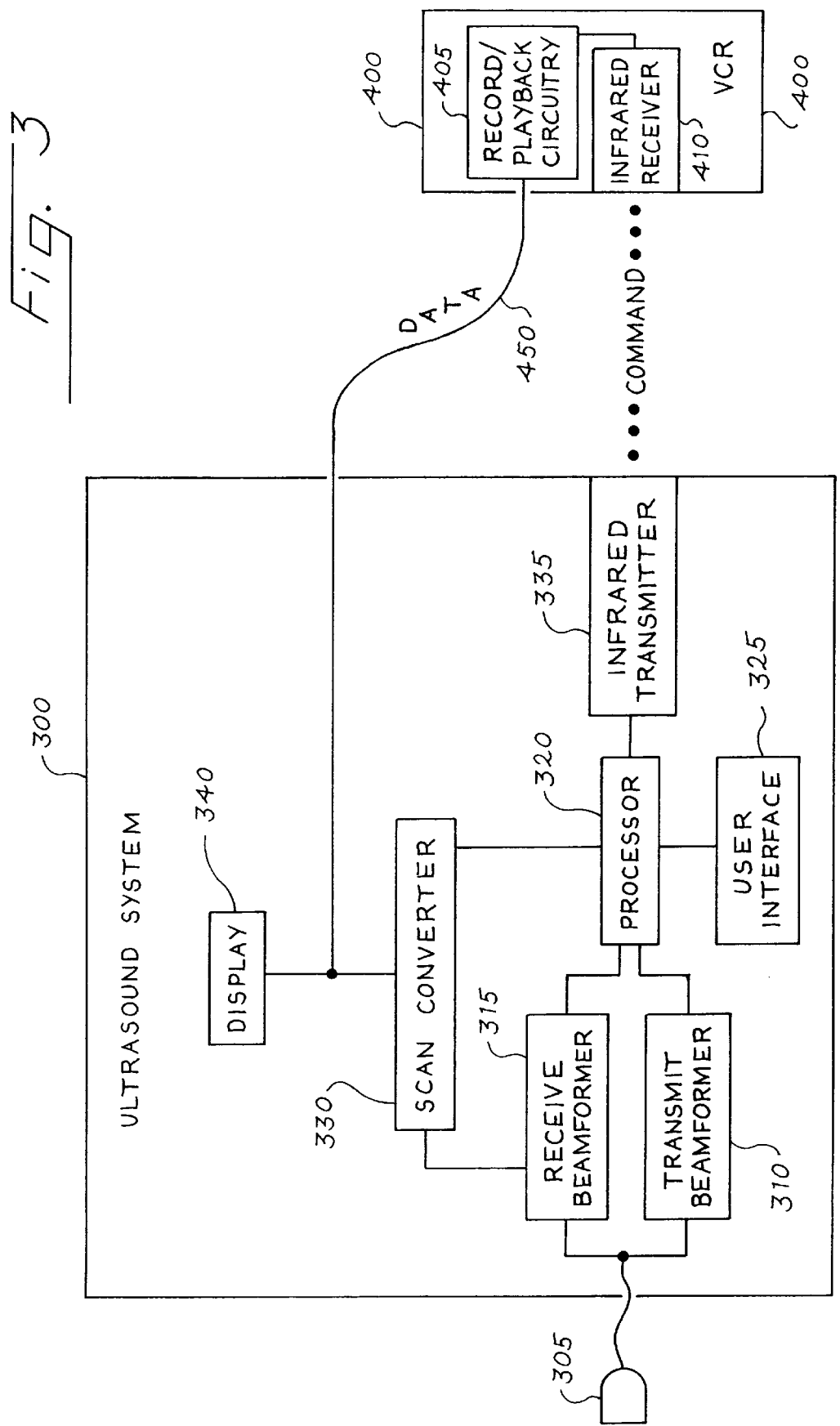
FIG. 3 is a block diagram of a medical diagnostic ultrasound imaging system and an ultrasound system peripheral of another preferred embodiment.

Turning now to the drawings, FIG. 1 is a block diagram of a medical diagnostic ultrasound imaging system 10 and ultrasound system peripheral 100 of a presently preferred embodiment. As used herein, the term "ultrasound system peripheral" broadly refers to any device that can be used with an ultrasound system. A peripheral can be, for example, a video recording device, a video playback device, a video cassette recorder (VCR), a DVD player and/or recorder, a printer, a multi-image camera, a strip-chart recorder, a tape recorder, a desktop computer, a laptop computer, a handheld computer, or a robot.

As shown in FIG. 1, the ultrasound system 10 comprises a first data channel 20 and a first wireless communication device 30. The ultrasound system peripheral 100 comprises a second data channel 120 and a second wireless communication device 130. The first and second data channels 20, 120 are physically coupled with a data transmission medium 50, through which data is transmitted between the ultrasound system 10 and peripheral 100. As used herein, the term "coupled with" means directly coupled with or indirectly coupled with through one or more components. Also as used herein, the term "data transmission medium" is used to refer to any type of medium that can be used to physically couple the ultrasound system 10 with the peripheral 100 and that can transmit data therebetween. Examples of a data transmission medium include, but are not limited to, one or more wires, a single- or multi-wire cable, and a fiber optics connector.

A preferred method for transmitting data and peripheral commands between the ultrasound system 10 and peripheral 100 is shown in the flow chart 200 of FIG. 2. As shown in the flow chart 200, data is transmitted between the ultrasound system 10 and the ultrasound system peripheral 100 via the data transmission medium 50 that physically couples the ultrasound system 10 and the peripheral 100 (act 210).

(In this preferred embodiment, commands are not sent via the data transmission medium 50.) Before, during, and/or after act 210, a peripheral command is wirelessly transmitted from the ultrasound system 10 to the peripheral 100 (act 220). (In this preferred embodiment, data is not wirelessly transmitted between the ultrasound system 10 and peripheral 100.) Then, the peripheral performs an operation in response to receipt of the peripheral command (act 230). It should be noted that an ultrasound peripheral operation can be any operation or function that is performable by the peripheral. For example, a peripheral can be preprogrammed with one or more operations that are performed in response to the receipt of a command to perform the operation(s). The term "peripheral command" is used herein to refer to any command that, upon receipt by the peripheral, causes the peripheral to perform an operation.

There are several advantages associated with this preferred embodiment. First, because a single wireless communication device on the ultrasound system 10 can communicate with a several peripherals, the physical-resource limitation of current configurations, which require a command port on the ultrasound system for each peripheral used, is virtually eliminated. In addition to allowing more peripheral devices to be used, the reduction in the number of command ports can also reduce the cost of the ultrasound system. Also, because a separate command port is not needed, this preferred embodiment allows less expensive, consumer-grade peripherals, which are typically commodity products purchased through retail channels, to be used. Because these types of peripherals typically do not have a wired or hard-wired command port (e.g., a RS-232 port), these preferred embodiments allow the control of peripherals that were, when used, previously not controlled by the ultrasound system. In one illustrative application, a low-cost, consumer-grade VCR with an integral infrared receiver for receiving control signals can be used instead of a more expensive, specialized VCR with a separate RS-232 command port. This illustrative application will now be described in more detail with reference to FIG. 3.

FIG. 3 is a block diagram of a medical diagnostic ultrasound imaging system 300 and ultrasound system peripheral 400 that illustrates one preferred implementation of the ultrasound system and peripheral shown in FIG. 1. The ultrasound system 300 comprises a transducer 305, which is coupled with a transmit beamformer 310 and a receive beamformer 315. The beamformers 310, 315 are each coupled with a processor 320, which is coupled with a user interface 325, a scan converter 330, and an infrared transmitter 335. The term "processor" broadly refers to any appropriate hardware and/or software component of the ultrasound system 300 that can be used to implement the preferred embodiments described herein. It should be understood that any appropriate hardware (analog or digital) or software can be used and that the embodiments described herein can be implemented exclusively with hardware. Further, the processor 320 can be separate from or combined with (in part or in whole) other processors of the ultrasound system 300 (including attendant processors), which are not shown in FIG. 3 for simplicity. The processor 320 can also include a memory device that stores software executable by the processor 320.

In operation, the processor 320 causes the transmit beamformer 310 to apply a voltage to the transducer 305 to cause it to vibrate and emit an ultrasonic beam into an object, such as human tissue (i.e., a patient's body). Ultrasonic energy reflected from the body impinges on the transducer 305, and the resulting voltages created by the transducer 305 are received by the receive beamformer 315. The scan converter 330, under control of the processor 320, processes the sensed voltages to create an ultrasound image associated with the reflected signals and displays the image on a display 340. The user interface 325 can be used, for example, to adjust parameters used in the transmit, receive, and display operations. It should be noted that the ultrasound imaging system 300 can comprise additional components.

The ultrasound system peripheral 400 of this presently preferred embodiment takes the form of a VCR. The VCR 400 comprises conventional record/playback circuitry 405 and an infrared receiver 410. In operation, data is sent between the ultrasound system 300 and VCR 400 via a data transmission medium 450, and peripheral commands are sent from the ultrasound system 300 to the peripheral 400 with the infrared transmitter 335 and are received by the peripheral 400 with the infrared receiver 410.

To illustrate the operation of this exemplary embodiment, consider the situation in which a user of the ultrasound system 300 desires to record an ultrasound image generated by the system 300. In this example, the user interface 325 is used to communicate the "record" request. The user interface 325 can be physically attached to the ultrasound system 300, such as when the user interface 325 is a CRT touch-screen or a key, knob, button, slide, switch, trackball, and/or voice input device of the ultrasound system's console. The user interface 325 can also be a remote control device dedicated to the ultrasound system (e.g., a wand or handheld controller), dedicated to the peripheral, or shared by the system and peripheral. For example, if the ultrasound system 300 has an infrared receiver and is sensitive to commands issued by the remote control of the VCR 400, the VCR's remote control can be used to send an operation request to both the ultrasound system 300 and the VCR 400.

Returning to the example, a user first presses a "record" button on the user interface 325. The processor 320 (or a microprocessor associated with the user interface 325) scans inputs from the user interface 325, and when it receives a key press, for example, to record an image, the processor 320 sends video data from the scan converter 330 to the record/playback circuitry 405 of the VCR 400. The processor 320 also determines the appropriate coded infrared signal to be transmitted for a "record" command and sends that signal to the infrared transmitter 335 for transmission. The command signal can be sent before, during, and/or after the transmission of data. When the VCR 400 receives the "record" command, the record/playback circuitry 405 records the video signal on videotape. In another application, after the user presses a "play" button, the processor 320 sends a "play" command to the VCR 400 via the infrared transmitter 335. Upon receipt of the "play" command, the VCR 400 sends video data to the ultrasound system 300 (either directly to the display 340 or indirectly through the scan converter 330) for display. Of course, the processor 320 may be issuing other internal or external commands during this operation. For example, before, during, and/or after the ultrasound system 300 wirelessly transmits a "play" command to the VCR 400, the processor 320 can switch video modes to allow the ultrasound system 300 to be able to display the incoming video data from the VCR 400.

As shown in the example described above, the processor 320 can be responsible for translating a peripheral operation requested via the user interface 325 to a peripheral command. As shown in FIG. 4, the processor 320 can execute a peripheral interface, which is, in this example, a look-up table that correlates operations requested by the ultrasound system 300 with infrared signals understood by the VCR 400. For example, if a "record" operation is requested, the look-up table is indexed with the "record" request to determine the appropriate infrared signal to be sent to the infrared transmitter 335 for transmission. In addition to translating information received by the ultrasound system, the same or a different peripheral interface can be used to translate information sent to the system by the peripheral. For example, the peripheral interface can be used to translate coded infrared signals (such as operational status, tape status, counter information, etc.) received from the VCR.

Because different peripherals can use different infrared signals (i.e., peripheral commands), the processor 320 can have a device library with a plurality of peripheral interfaces, each associated with a particular peripheral, as shown in FIG. 5. In this way, the ultrasound system 300 first identifies which peripheral it wants to control (the "library choice"), and then translates the requested operation into a peripheral command using the selected peripheral interface. For example, the device library can store peripheral interfaces for different VCR manufacturers so that the ultrasound system will be able to communicate with any one of a number of VCRs without user input of device-specific control codes. In another preferred embodiment, a peripheral can transmit (wirelessly or via the data transmission medium 450) an identification code that the ultrasound system can use to automatically select a peripheral interface from a device library. Also, while peripheral interfaces can be pre-installed in the ultrasound system, they can also be updated via, for example, a modem connection. Further, smart controllers can be used to learn the requirements of a particular peripheral device, reducing the need for upgrades to the device library.

It should be noted that while the above examples were discussed in terms of an operation requested by a user via a user interface, the requested command can also be issued by the ultrasound system itself, such as when an operation is automatically requested by the system. For example, the ultrasound system can be programmed to automatically request a "record" operation in response to the occurrence of a selected imaging mode.

In the above example, the peripheral interface was described as a software application executed by the processor 320. The peripheral interface functionality can also be implemented as hardware, separate from or part of the processor 320. For example, an EPROM, NVRAM, or NOVRAM programmed with the peripheral interface functionality can be used. As another example, a separate infrared control integrated circuit can be used. One suitable integrated circuit is the IC4001™ universal infrared control integrated circuit from Innotech Systems Inc. (Port Jefferson, N.Y.), which includes a device library with peripheral interfaces for several VCRs.

In another preferred embodiment, a medical diagnostic ultrasound imaging system comprises a housing that has an integral wireless communication device and a storage location defined by the housing and adapted to store an ultrasound system peripheral. The storage location and the wireless communication device are positioned in the housing to allow wireless communication between the wireless communication device and a wireless communication device of a peripheral stored in/by the storage location. For example, when the wireless communication device communicates with infrared transmissions, it is preferred that the storage location and the wireless communication device be positioned in the housing to provide an unimpeded optical path between the wireless communications device of the housing and the wireless communication device of the peripheral stored in the storage location. FIGS. 6–8 illustrate this embodiment.

In FIG. 6, the storage location is the top surface of the housing 610, and the ultrasound peripheral is a forward-facing VCR 620 with an infrared receiver. The housing 610 comprises an infrared transmitter 630 integral with the housing 610 and coupled with a processor (not shown). This arrangement provides an unimpeded optical path between the infrared transmitter 630 of the housing 610 and the infrared receiver of the VCR 620. FIG. 6 also shows other suitable locations 622, 624, 626 on the ultrasound system's console for the infrared transmitter. In FIG. 7, the VCR 720 is side facing, and the infrared transmitter 730 is located adjacent the VCR 720 when the VCR 720 is stored on the top surface of the housing 710. In FIG. 8, forward-facing and side-facing VCRs 820, 825 are stored in two openings within the housing 810. Infrared transmitters 830, 835 mounted in the housing 810 are located near the infrared receivers of the VCRs 820, 825.

FIG. 9 is an illustration showing one preferred way in which an infrared transmitter can be integrally mounted to the housing. In FIG. 9, the infrared transmitter 910 is coupled with the ultrasound system's processor (not shown) with a cable 915. An infrared lens 920 is mounted over the transmitter 910 to aim infrared transmission to an infrared receiver of a forward-facing VCR 925.

There are many alternatives to the embodiments described above. For example, in the embodiments illustrated above, the command sent to the peripheral caused the peripheral to perform a function related to the data sent between the ultrasound system and peripheral. In one alternate embodiment, the function performed by a peripheral in response to a command is not associated with data sent between the ultrasound system and peripheral, if data is sent at all (such as when a "fast forward" command is sent). In another alternate embodiment, when a plurality of peripherals is used, one or more wireless communication devices can be used by the ultrasound system to communicate with the peripherals. Further, it is important to note that any of the various aspects of any of the preferred embodiments can be used alone or in combination.

Additionally, as mentioned above, in addition to or as an alternative to the ultrasound system sending a peripheral command to the peripheral, the peripheral can send an ultrasound system command to the ultrasound system. This allows for bi-directional control between the ultrasound system and peripheral. When the ultrasound system receives the ultrasound system command, it performs an ultrasound system operation associated with the command. The ultrasound system can have a peripheral interface (or a device library of peripheral interfaces) to translate the ultrasound system command into an ultrasound system operation. It should be noted that an ultrasound system operation can be any operation or function that is performable by the ultrasound system. In reference to the example described above, the "ultrasound system operation" can simply be the selection of a peripheral interface in response to the ultrasound system receiving a "command" from the peripheral identifying its model type. The term "ultrasound system command" is used herein to refer to any command that, upon receipt by the ultrasound system, causes the ultrasound system to perform an operation.

In an alternate embodiment, a medical diagnostic ultrasound imaging system with a first wireless communication device is used to transmit a peripheral command via the first wireless communication device to an ultrasound system peripheral. In this embodiment, the ultrasound system peripheral has a second wireless communication device that is integral with the peripheral (ie., the peripheral and the second wireless communication device are in the same housing). As with the above embodiments, the ultrasound system peripheral is operative to perform an operation in response to receipt, via the second wireless communication device, of the peripheral command. In this alternate embodiment, the use of a data transmission medium to physically couple and communicate data between the ultrasound system and the peripheral is optional.

For simplicity, the term "wireless communication device" has been used to broadly refer to any device that has the ability to transmit information, preferably an ultrasound peripheral command, from one point to another without the use of a physical connection. The wireless communication device can be integral with the ultrasound system or peripheral, such as when the peripheral contains a built-in infrared receiver. The wireless communication device can also be an add-on component to the ultrasound system or peripheral, such as when the wireless communication device 1010 of the ultrasound system 1000 is a detachable accessory that is tethered to the system, as shown in FIG. 10. A wireless communication device can include an emitter, receiver, or transceiver. In some applications, it is preferred that the wireless communication device be able to communicate virtually simultaneously in receive and transmit modes (e.g., by time-slicing between operations) and be able to communicate virtually simultaneously with more than one peripheral device (e.g., by time-slicing between peripheral devices).

Example of wireless communication devices include, but are not limited to, devices that communicate information using infrared, radio frequency, light wave, microwave, or ultrasonic transmissions. Examples of suitable infrared detectors (e.g., photo diodes or photo transistors) include part number BPW82 from Vishay Telefunken (Basking Ridge, N.J.), part number HSPL-5400 from Hewlett-Packard (Palo Alto, Calif.), and part number SFH320 from Infineon Technologies (Munich, Germany). The detector can also take the form of an infrared photomodule, such as part number TSOP1838 from Vishay Telefunken and part number SFH5110 from Infineon Technologies. Examples of suitable infrared emitters include part number TSAL6200 from Vishay Telefunken, part number HSPL-4200 from Hewlett-Packard, and part number SFH426 from Infineon Technologies.

In one embodiment, the peripheral is compatible with the IrDA infrared communication protocol developed by the Infrared Data Association. IrDA peripheral devices provide a walk-up, point-to-point method of data transfer that is adaptable to a broad range of computing and communication devices. Version 1.1 of the IrDA infrared communication protocol provides for communication at data rates up to 4 Megabytes per second. The IrDA infrared communication protocol also defines a set of specifications, or protocol stack, that provides for the establishment and maintenance of a link so that error free communication is possible. Devices that are compatible with the IrDA infrared communication protocol presently include: I/O controllers, transceivers, receivers, encoder boards, notebook/portable/desktop computers, handheld personal data assistants (PDAs), adapters, printers, telephones, network access equipment, modems, keyboards, computer mice and other remote control devices. Examples of suitable types of IrDA Data Compliant infrared transceivers are part number TFDT6501E from Vishay Telefunken, part number HSPL-3610 from Hewlett-Packard and part number IRMT6400 from Infineon Technologies.

The following two patent applications assigned to the assignee of the present invention relate to wireless transmissions and are hereby incorporated by reference: "Diagnostic Medical Ultrasound System with Wireless Communication Device"(U.S. Application Ser. No. 09/237,548; filed Jan. 26, 1999) and "Medical Diagnostic Ultrasound Imaging System and Method for Transferring Ultrasound Examination Data to a Portable Computing Device"(U.S. Application Ser. No. 09/538,320; filed on the same day as the present patent application).

It is intended that the foregoing detailed description be understood as an illustration of selected forms that the invention can take and not as a definition of the invention. It is only the following claims, including all equivalents, that are intended to define the scope of this invention.

What is claimed is:

1. A medical diagnostic ultrasound imaging system and peripheral comprising:

a medical diagnostic ultrasound imaging system comprising a first wireless communication device, the medical diagnostic ultrasound imaging system operative to transmit a peripheral command via the first wireless communication device;

an ultrasound system peripheral comprising a second wireless communication device, the ultrasound system peripheral being operative to perform an operation in response to receipt, via the second wireless communication device, of the peripheral command; and a data transmission medium physically coupling the medical diagnostic ultrasound imaging system and the ultrasound system peripheral, the data transmission medium being operative to communicate data between the medical diagnostic ultrasound imaging system and the ultrasound system peripheral.

2. The invention of claim 1, wherein the medical diagnostic ultrasound imaging system further comprises a peripheral interface in communication with the first wireless communication device, the peripheral interface operative to translate a peripheral operation request into the peripheral command.

3. The invention of claim 2, wherein the peripheral interface comprises a look-up table.

4. The invention of claim 2, wherein the peripheral interface comprises an infrared control integrated circuit.

5. The invention of claim 1, wherein the medical diagnostic ultrasound imaging system further comprises a plurality of peripheral interfaces, and wherein the medical diagnostic ultrasound imaging system is further operative to select a peripheral interface from said plurality of peripheral interfaces and to translate a peripheral operation request into the peripheral command using the selected peripheral interface.

6. The invention of claim 1, wherein the ultrasound system peripheral is further operative to transmit an ultrasound system command via the second wireless communication device, and wherein the medical diagnostic ultrasound imaging system is further operative to perform an ultrasound system operation in response to receipt, via the first wireless communication device, of the ultrasound system command.

7. The invention of claim 6, wherein the medical diagnostic ultrasound imaging system further comprises a peripheral interface in communication with the first wireless communication device, the peripheral interface operative to translate the ultrasound system command into an ultrasound system operation.

8. The invention of claim 6, wherein the medical diagnostic ultrasound imaging system further comprises a plurality of peripheral interfaces, and wherein the medical diagnostic ultrasound imaging system is further operative to select a peripheral interface from said plurality of peripheral interfaces and to translate the ultrasound system command into an ultrasound system operation using the selected peripheral interface.

9. A method of transmitting data and commands between a medical diagnostic ultrasound imaging system and an ultrasound system peripheral, the method comprising:

(a) transmitting data between a medical diagnostic ultrasound imaging system and an ultrasound system peripheral via a data transmission medium that physically couples the medical diagnostic ultrasound system and the ultrasound system peripheral;

(b) wirelessly transmitting a peripheral command from the medical diagnostic ultrasound imaging system to the ultrasound system peripheral; and (c) with the ultrasound system peripheral, performing an operation in response to receipt of the peripheral command.

10. The invention of claim 9 further comprising translating a peripheral operation request into the peripheral command.

11. The invention of claim 9 further comprising:

selecting a peripheral interface from a plurality of peripheral interfaces of the medical diagnostic ultrasound imaging system; and translating a peripheral operation request into the peripheral command using the selected peripheral interface.

12. The invention of claim 9 further comprising:

transmitting an ultrasound system command via the second wireless communication device; and with the ultrasound imaging system, performing an ultrasound system operation in response to receipt, via the first wireless communication device, of the ultrasound system command.

13. The invention of claim 12 further comprising translating the ultrasound system command into an ultrasound system operation.

14. The invention of claim 12 further comprising:

selecting a peripheral interface from a plurality of the peripheral interfaces; and with the selected peripheral interface, translating the ultrasound system command into an ultrasound system operation.

15. A medical diagnostic ultrasound imaging system comprising a first wireless communication device, the ultrasound system being for use with an ultrasound peripheral comprising a second wireless communication device and comprising:

a housing;

a storage location defined by the housing and adapted to store an ultrasound system peripheral;

a processor housed within the housing; and a first wireless communication device coupled with the processor and integral with the housing;

wherein the storage location and the first wireless communication device are positioned in the housing to allow wireless communication between the first wireless communication device and a second wireless communication device of an ultrasound peripheral stored in the storage location.

16. The invention of claim 15, wherein the storage location comprises a top surface of the housing.

17. The invention of claim 15, wherein the storage location is defined by an opening formed within the housing.

18. A medical diagnostic ultrasound imaging system and peripheral comprising:

a medical diagnostic ultrasound imaging system comprising a first wireless communication device, the medical diagnostic ultrasound imaging system operative to transmit a peripheral command via the first wireless communication device;

an ultrasound system peripheral comprising a second wireless communication device integral with the ultrasound system peripheral, the ultrasound system peripheral being operative to perform an operation in response to receipt, via the second wireless communication device, of the peripheral command.

19. The invention of claim 18 further comprising a data transmission medium physically coupling the medical diagnostic ultrasound imaging system and the ultrasound system peripheral, the data transmission medium being operative to communicate data between the medical diagnostic ultrasound imaging system and the ultrasound system peripheral.

20. The invention of claim 18, wherein the medical diagnostic ultrasound imaging system further comprises a peripheral interface in communication with the first wireless communication device, the peripheral interface operative to translate a peripheral operation request into the peripheral command.

21. The invention of claim 20, wherein the peripheral interface comprises a look-up table.

22. The invention of claim 20, wherein the peripheral interface comprises an infrared control integrated circuit.

23. The invention of claim 18, wherein the medical diagnostic ultrasound imaging system further comprises a plurality of peripheral interfaces, and wherein the medical diagnostic ultrasound imaging system is further operative to select a peripheral interface from said plurality of peripheral interfaces and to translate a peripheral operation request into the peripheral command using the selected peripheral interface.

24. The invention of claim 18, wherein the ultrasound system peripheral is further operative to transmit an ultrasound system command via the second wireless communication device, and wherein the medical diagnostic ultrasound imaging system is further operative to perform an ultrasound system operation in response to receipt, via the first wireless communication device, of the ultrasound system command.

25. The invention of claim 24, wherein the medical diagnostic ultrasound imaging system further comprises a peripheral interface in communication with the first wireless communication device, the peripheral interface operative to translate the ultrasound system command into an ultrasound system operation.

26. The invention of claim 24, wherein the medical diagnostic ultrasound imaging system further comprises a plurality of peripheral interfaces, and wherein the medical diagnostic ultrasound imaging system is further operative to select a peripheral interface from said plurality of peripheral interfaces and to translate the ultrasound system command into an ultrasound system operation using the selected peripheral interface.

27. The invention of claim 1, 9, 15, or 18, wherein the first wireless communication device is a wireless transmitter, and wherein the second wireless communication device is a wireless receiver.

28. The invention of claim 1, 9, 15, or 18, wherein the first wireless communication device is an infrared transmitter, and wherein the second wireless communication device is an infrared receiver.

29. The invention of claim 1, 9, 15, or 18, wherein at least one of the first and second wireless communication devices comprises a wireless transceiver.

30. The invention of claim 1, 9, 15, or 18, wherein the second wireless communication device is integral with the ultrasound system peripheral.

31. The invention of claim 1, 9, 15, or 18, wherein the second wireless communication device and the ultrasound system peripheral are housed in separate housings.

32. The invention of claim 1, 9, 15, or 18, wherein the first and second wireless communication devices communicate via a transmission selected from the group consisting of infrared, radio frequency, light wave, microwave, and ultrasonic transmissions.

33. The invention of claim 1, 9, 15, or 18, wherein the ultrasound system peripheral comprises a peripheral selected from the group consisting of a video recording device, a video playback device, a video cassette recorder (VCR), a DVD player and/or recorder, a printer, a multi-image camera, a strip-chart recorder, tape recorders, desktop computer, laptop computer, handheld computer, and robot.

34. The invention of claim 1, wherein the first wireless communication device is integral with the ultrasound system.

35. The invention of claim 1, wherein the first wireless communication device and the ultrasound system are housed in separate housings and the first wireless communication device is tethered to the ultrasound system with a cable.

* * * * *